United States Patent
Kobayashi et al.

(10) Patent No.: US 9,526,444 B2
(45) Date of Patent: Dec. 27, 2016

(54) BIOLOGICAL SIGNAL MEASURING APPARATUS AND BIOLOGICAL SIGNAL MEASURING METHOD

(75) Inventors: Naoki Kobayashi, Tokyo (JP); Kazumasa Ito, Tokyo (JP); Hideaki Hirahara, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 931 days.

(21) Appl. No.: 13/292,269

(22) Filed: Nov. 9, 2011

(65) Prior Publication Data
US 2012/0130211 A1 May 24, 2012

(30) Foreign Application Priority Data

Nov. 9, 2010 (JP) .................................. 2010-250684
Oct. 4, 2011 (JP) .................................. 2011-220125

(51) Int. Cl.
| A61B 5/1455 | (2006.01) |
| A61B 5/00 | (2006.01) |
| A61B 5/02 | (2006.01) |
| A61B 5/024 | (2006.01) |
| A61B 5/022 | (2006.01) |

(52) U.S. Cl.
CPC ......... *A61B 5/14551* (2013.01); *A61B 5/0059* (2013.01); *A61B 5/02028* (2013.01); *A61B 5/02416* (2013.01); *A61B 5/6826* (2013.01); *A61B 5/02241* (2013.01); *A61B 5/6838* (2013.01)

(58) Field of Classification Search
CPC .............. A61B 5/1455; A61B 5/14551; A61B 5/14552; A61B 5/02; A61B 5/02007; A61B 5/6826; A61B 5/7271

USPC ............... 600/310, 322, 323, 324, 335, 502
See application file for complete search history.

(56) References Cited

U.S. PATENT DOCUMENTS

| 2002/0115935 A1 | 8/2002 | Shani et al. |
| 2005/0070774 A1 | 3/2005 | Addison et al. |
| 2007/0282182 A1 | 12/2007 | Messerges et al. |
| 2009/0143655 A1 | 6/2009 | Shani |

OTHER PUBLICATIONS

Japanese Office Action for the related Japanese Patent Application No. 2011-220125 dated Sep. 24, 2014.

(Continued)

*Primary Examiner* — Eric Winakur
(74) *Attorney, Agent, or Firm* — Pearne & Gordon LLP

(57) ABSTRACT

A biological signal measuring apparatus includes: a light emitter which emits at least two light beams having different wavelengths to living tissue of a subject; a light receiver which receives the light beams that are emitted from the light emitter, and which converts at least one of the light beams to at least one electric signal that corresponds to a reception light intensity of the at least one of the light beams; a detector which detects temporal variation of the reception light intensity from the electric signal; a selector which selects a pulse oximeter mode in which at least one of an oxygen saturation and a pulse rate is calculated and a capillary refilling time measurement mode in which a capillary refilling time is calculated; and a calculator which, based on the temporal variation of the reception light intensity, performs a calculation in the mode selected by the selector.

17 Claims, 9 Drawing Sheets

(56) References Cited

OTHER PUBLICATIONS

Walter Karlen et al.; "Automated Validation of Capillary Refill Time Measurements Using Photo-plethysmogram from a Portable Device for Effective Triage in Children"; Global Humanitarian Technology Conference (GHTC); Oct. 30, 2011; pp. 66-71; XP032074363.
European Search Report for related European Application No. 11188290.8-1526 dated Feb. 17, 2012.
European Office Action for the related European Patent Application No. 11 188 290.8 dated Feb. 6, 2015.
Chinese Office Action for the related Chinese Patent Application No. 201110353682.0 dated Jun. 30, 2015.

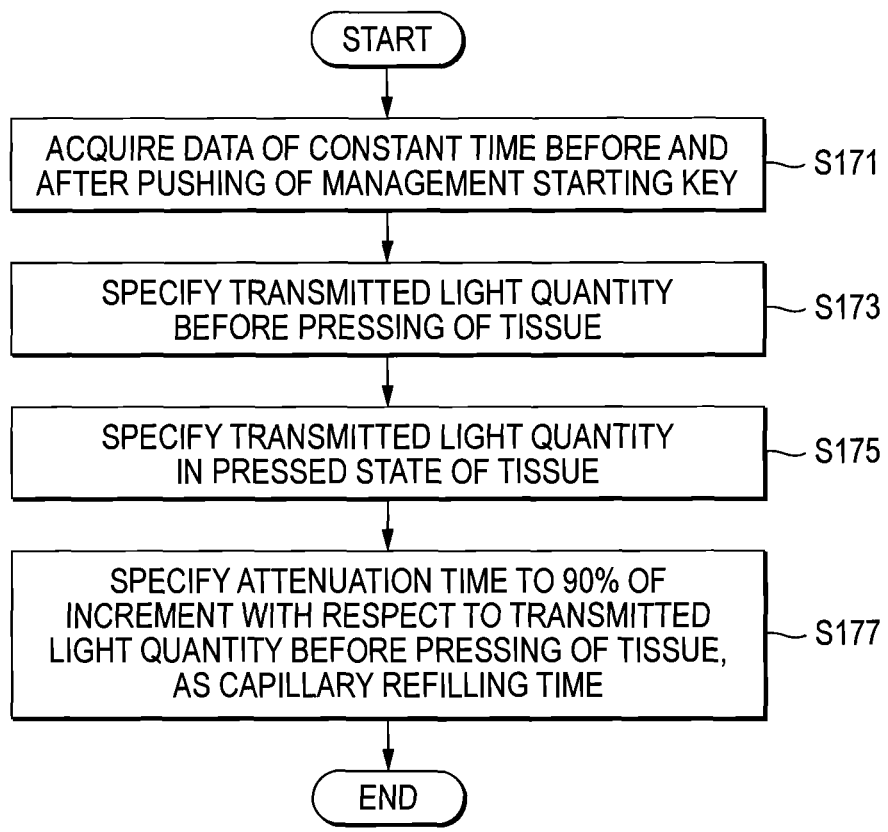

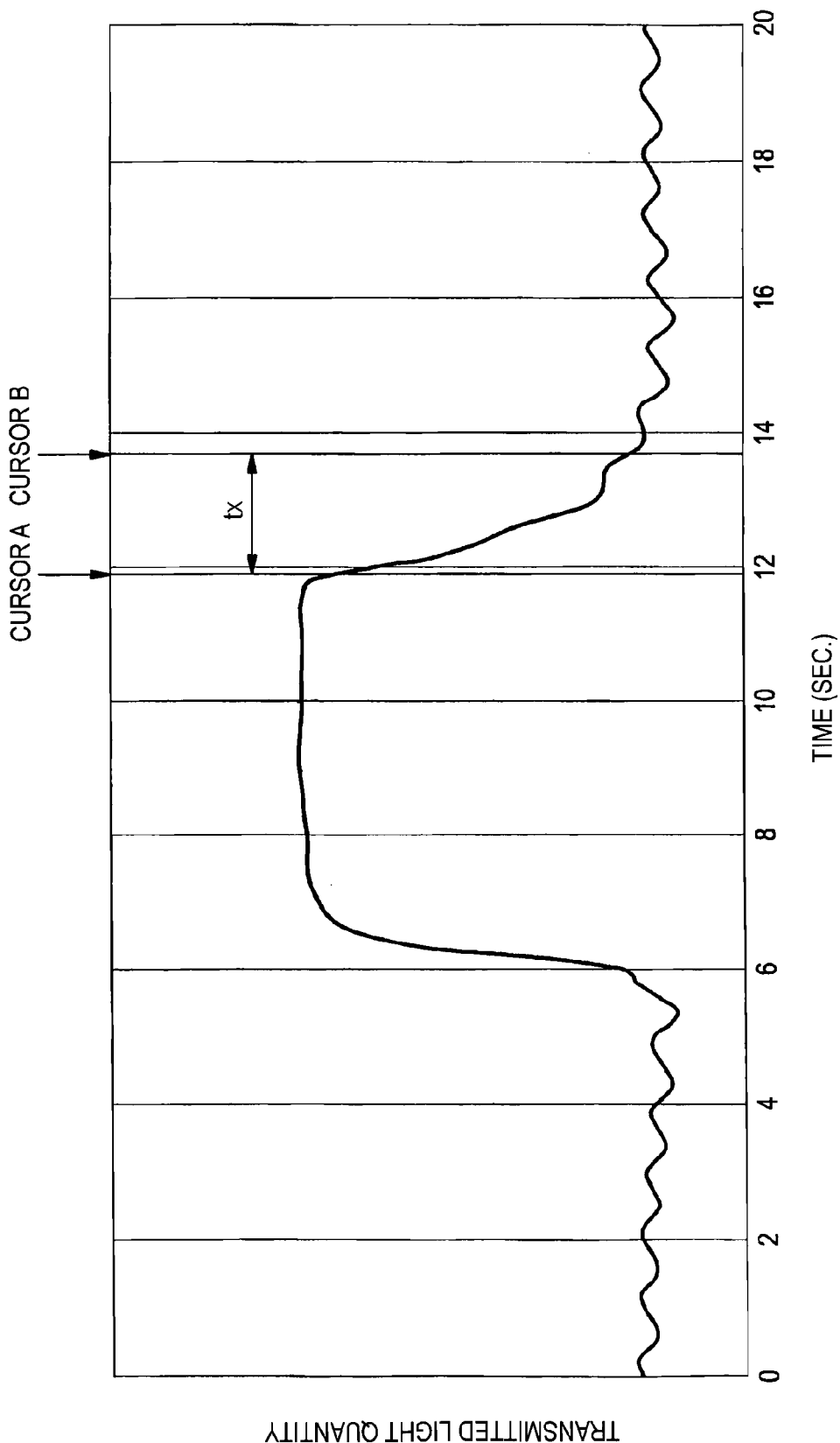

BIOLOGICAL SIGNAL MEASURING APPARATUS AND BIOLOGICAL SIGNAL MEASURING METHOD

BACKGROUND OF THE INVENTION

The present invention relates to a pulse oximeter and a method of measuring the capillary refilling time, and more particularly to a pulse oximeter which, in addition to a calculation function that is provided in a related-art pulse oximeter and that calculates the blood oxygen saturation of an artery or the pulse rate based on pulse waves acquired from periodic variation components of the reception light intensities in the case where at least two light beams of different wavelengths are transmitted through or reflected from living tissue, includes a calculator that detects variations of the reception light intensities due to release of a state where the living tissue is pressed and that calculates the capillary refilling time, and also to a method of measuring the capillary refilling time.

In a related art, the capillary refilling time (CRT) is acquired in the manner in which a finger tip of the subject is pressed, the pressing is then released, the color of the skin after releasing is visually checked, and the time elapsed until the original color is regained is measured. However, such a visual measurement has poor quantitative performance, and an error due to a user easily occurs. Therefore, an apparatus has been proposed in which a finger tip is inserted into a probe having a clip-like shape, the finger tip is pressed by an actuator incorporated in the probe, and, when the pressing is then released, the capillary refilling time is detected (see U.S. Patent Application Publication No. 2007/0282182).

The measurement of the capillary refilling time is often performed in an emergency situation such as a case where an unconscious patient is transported by ambulance, and therefore easiness of measurement, and operation in parallel with other measurement are required in addition to measurement accuracy. In the related-art apparatus disclosed in U.S. Patent Application Publication No. 2007/0282182, although special devices such as the actuator is necessary and therefore preparation for measurement and measurement itself require a prolonged time, the possible measurement is substantially limited only to measurement of the capillary refilling time. Therefore, the apparatus is not popularly used at emergency sites where an emergency medical person is accustomed to performing rapid visual measurement.

SUMMARY

According to the invention, there is provided a biological signal measuring apparatus comprising: a light emitter which emits at least two light beams having different wavelengths to living tissue of a subject; a light receiver which receives the light beams that are emitted from the light emitter and transmitted through or reflected from the living tissue, and which converts at least one of the light beams to at least one electric signal that corresponds to a reception light intensity of the at least one of the light beams; a detector which detects temporal variation of the reception light intensity from the electric signal; a selector which selects a pulse oximeter mode in which at least one of an oxygen saturation and a pulse rate is calculated and a capillary refilling time measurement mode in which a capillary refilling time is calculated; and a calculator which, based on the temporal variation of the reception light intensity, performs a calculation in the mode that is selected by the selector.

The selector may select only one of the pulse oximeter mode and the capillary refilling time measurement mode.

The calculator may detect that the living tissue is released from a pressed state in which the living tissue is pressed, in accordance with that a level of the reception light intensity or a time differential of a temporal reduction of the reception light intensity becomes less than a predetermined threshold.

In a case where the capillary refilling time measurement mode is selected, the calculator may calculate, as the capillary refilling time, a time which, after detecting that the living tissue is released from the pressed state, is required for the reception light intensity to be reduced to a predetermined rate with respect to a difference between levels of the reception light intensity before and after the living tissue is pressed.

The calculator may average a variation of the reception light intensity in a predetermined time in each of the pressed state and a state before the living tissue is pressed, and calculate, as the difference, a difference between the averaged variation in the pressed state and the averaged variation in the state before the living tissue is pressed.

The calculator may apply notch filtering centered at frequency components of a pulse wave on a variation of the reception light intensity in a predetermined time.

The calculator may change a detection sensitivity of the electric signal so that the electric signal can be detected in the pressed state, in accordance with that a level of the reception light intensity or a time differential of a temporal increase of the reception light intensity exceeds a predetermined threshold.

The biological signal measuring apparatus may further comprise an operation acceptor which accepts an operation of starting measurement of the capillary refilling time. The calculator may change a detection sensitivity of the electric signal so that the electric signal can be detected in the pressed state, in accordance with that the operation acceptor accepts the operation of starting measurement of the capillary refilling time.

The calculator may maintain the detection sensitivity constant during a period from a time when the detection sensitivity is changed to a time when the capillary refilling time is calculated.

The biological signal measuring apparatus may further comprise a display which displays the capillary refilling time and the temporal variation of the reception light intensity.

In a case where a plurality of the capillary refilling time are calculated, under a condition that one of the plurality of the capillary refilling time which is newly calculated satisfies a predetermined reject condition, the calculator may display an average of the other of the plurality of the capillary refilling time, as a latest capillary refilling time on the display.

The display may display a time waveform indicating the temporal variation of the reception light intensity and information for selecting time width corresponding to a part of the time waveform, and the calculator may calculate the time width based on the information displayed on the display.

In a case where the detection sensitivity is changed, the calculator may correct the temporal variation of the reception light intensity before the detection sensitivity is changed to the temporal variation of the reception light intensity after the detection sensitivity is changed.

The biological signal measuring apparatus may further comprise an instructing unit which provides an instruction of at least one of a timing when the living tissue is pressed and a timing when a pressed state in which the living tissue is pressed is released, to a user by a visual or auditory manner.

The biological signal measuring apparatus may further comprise a pressure sensor which detects at least one of a timing when the living tissue is pressed and a timing when a pressed state in which the living tissue is pressed is released. The calculator may perform the calculation based on the temporal variation of the reception light intensity and the timing that is detected by the pressure sensor.

According to the invention, there is also provided a method of measuring a biological signal, the method comprising: emitting at least two light beams having different wavelengths to living tissue of a subject; receiving the light beams transmitted through or reflected from the living tissue; converting at least one of the light beams to at least one electric signal that corresponds to a reception light intensity of the at least one of the light beams; detecting temporal variation of the reception light intensity from the electric signal; selecting a pulse oximeter mode in which at least one of an oxygen saturation and a pulse rate is calculated and a capillary refilling time measurement mode in which a capillary refilling time is calculated; and performing a calculation in the selected mode based on the temporal variation of the reception light intensity.

BRIEF DESCRIPTION OF THE DRAWINGS

FIG. 8 is a view showing an example of a flow of calculating the capillary refilling time by using the biological signal measuring apparatus.

FIG. 9 is a view showing an example of a screen of the display on which cursors for selecting time width $t_x$ are displayed together with the measurement waveform.

DETAILED DESCRIPTION OF EMBODIMENTS

Hereinafter, the invention will be described through an embodiment of the invention. The following embodiment is not intended to limit the invention defined in the appended claims. Moreover, all combinations of features described in the embodiment are not necessarily essential in the solving means of the invention.

Figure 1:
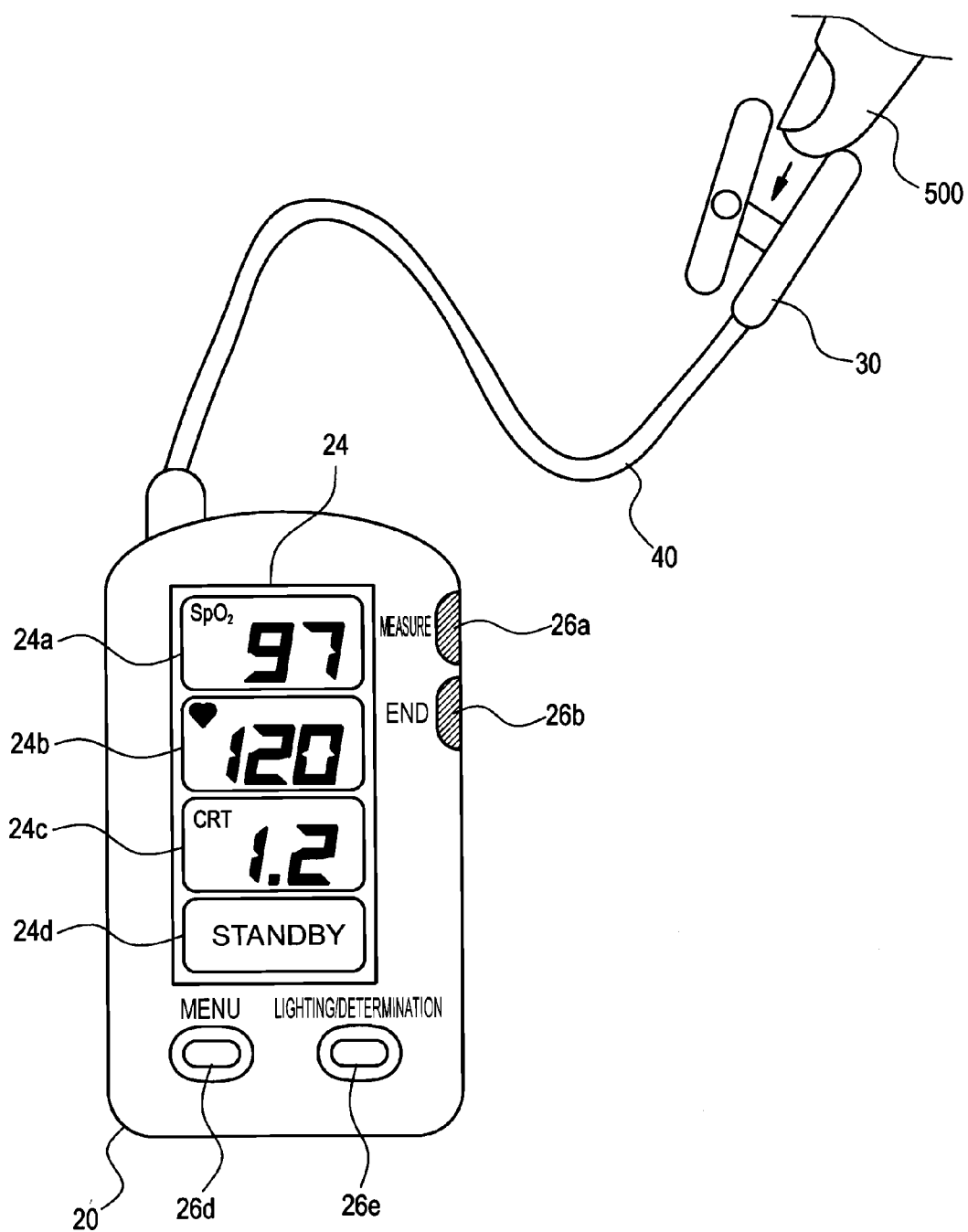
FIG. 1 is an external view of a biological signal measuring apparatus of an embodiment of the invention.
Figure 2:
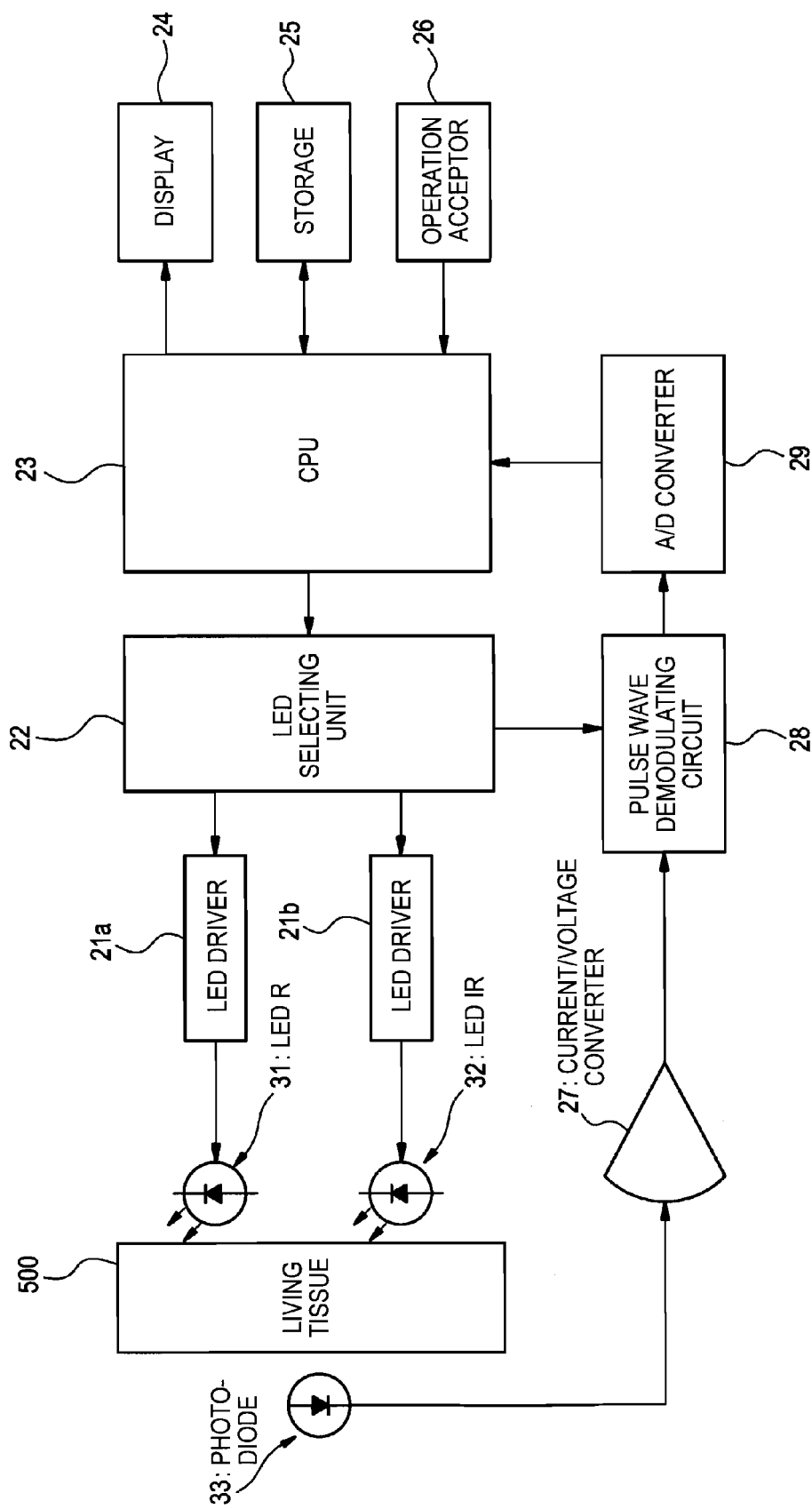
FIG. 2 is a schematic diagram of the biological signal measuring apparatus.

FIG. 1 is an external view of a biological signal measuring apparatus 10 of the embodiment of the invention, and FIG. 2 is a schematic diagram of the biological signal measuring apparatus 10. As shown in FIG. 1, the biological signal measuring apparatus 10 can measure biological signals of the subject such as the arterial oxygen saturation and the capillary refilling time, and includes an apparatus body unit 20, a probe 30, and a cable 40. As shown in FIG. 2, more specifically, the biological signal measuring apparatus 10 is configured by LED drivers 21a, 21b, an LED selecting unit 22, a CPU 23, a display 24, a storage 25, an operation acceptor 26, a current/voltage converter 27, a pulse wave demodulating circuit 28, an A/D converter 29, light emitting elements 31, 32, and a photodiode 33.

In the embodiment, among the components, the light emitting elements 31, 32 and the photodiode 33 are incorporated in the probe 30, and the other components are incorporated in the apparatus body unit 20. The cable 40 plays a role of transmitting signals between the components in the probe 30 and those in the apparatus body unit 20. The light emitting elements 31, 32 are examples of the light emitter in the invention, and the photodiode 33 is an example of the light receiver in the invention.

The light emitting element 31 (LED R) is a light emitting diode which is caused to emit light by a current supplied from the LED driver 21a, and the light emitting element 32 (LED IR) is a light emitting diode which is caused to emit light at a wavelength that is different from that of the light emitting element 31, by a current supplied from the LED driver 21b. In the embodiment, the light emitting element 31 emits red light (for example, a wavelength of 660 (nm)) which is more sensitive to a change of the arterial oxygen saturation, and the light emitting element 32 emits infrared light (for example, a wavelength of 940 (nm)) which is less affected by the arterial oxygen saturation.

The LED selecting unit 22 controls the LED drivers 21a, 21b so that the light emitting elements 31, 32 alternately emit light at predetermined intervals. The photodiode 33 receives light which is emitted from the light emitting elements 31, 32 toward living tissue 500 such as the finger of the subject inserted into the probe 30, to be transmitted through the living tissue 500, and converts the light to a current. In place of the configuration, a configuration may be employed where the photodiode 33 is disposed at a position where light which is emitted from the light emitting elements 31, 32 and reflected from the living tissue 500 can be received, so as to receive the light reflected from the living tissue 500.

The current/voltage converter 27 converts the current output from the photodiode 33, to a voltage signal (hereinafter, referred to as "electric signal"). The pulse wave demodulating circuit 28 receives a lighting timing signal indicative of lighting timings of the light emitting elements 31, 32, from the LED selecting unit 22, and, based on the lighting timing signal, divides the electric signal from the current/voltage converter 27 to electric signals respectively corresponding to reception light intensities of the red light (R) and infrared light (IR) which are received by the photodiode 33. The A/D converter 29 applies analog-digital conversion on the electric signals which correspond to the reception light intensities of the red light and the infrared light, respectively, and which are divided in the pulse wave demodulating circuit 28, and supplies the resulting signals to the CPU 23.

The CPU 23 controls portions of the biological signal measuring apparatus 10, and executes various calculation processes. Furthermore, the CPU 23 functions as the detector, selector, and calculator in the invention. Namely, the CPU 23 detects temporal variations of the reception light intensities of R light and IR light from the electric signals supplied from the A/D converter 29. During measurement of a biological signal, the CPU 23 selects one of a pulse oximeter mode and a capillary refilling time measurement mode in accordance with a manual operation by the user or an automatic operation (for example, with default setting). In the pulse oximeter mode, the CPU 23 calculates the blood oxygen saturation (arterial oxygen saturation) of the artery in the living tissue 500 and the pulse rate, and, in the capillary refilling time measurement mode, detects a variation of the reception light intensity of each light due to release from the state where the living tissue 500 is externally pressed, from the electric signals to calculate the capillary refilling time. The calculations will be described later in more detail.

The display 24 is a displaying device such as an LCD. As shown in FIG. 1, the display screen of the display is configured by: an arterial oxygen saturation display window 24a in which the arterial oxygen saturation in the living tissue 500 of the subject is displayed as a numeric value together with a display of "SpO$_2$"; a pulse rate display window 24b in which the pulse rate of the subject is displayed together with a heart-shaped symbol; a capillary refilling time display window 24c in which the capillary refilling time of the subject is displayed together with a display of "CRT"; and a status display window 24d in which, for example, various messages such as setting information of the biological signal measuring apparatus 10 are displayed.

The storage 25 may be one of related-art storage devices such as a flash memory or a hard disk drive, and stores control programs for controlling the biological signal measuring apparatus 10, and various measurement results calculated by the CPU 23. The operation acceptor 26 has a measurement button 26a, an end button 26b, a menu button 26d, and a lighting/determination button 26e.

In the biological signal measuring apparatus 10 of the embodiment, the pulse oximeter mode for measuring the arterial oxygen saturation (SpO$_2$) is set by default, and, when a power supply (not shown) is turned on, the measurement in the pulse oximeter mode is started. When the user pushes down the measurement button 26a, as described later, the biological signal measuring apparatus 10 is switched from the pulse oximeter mode to the capillary refilling time measurement mode, and measures the capillary refilling time of the subject. Also in the capillary refilling time measurement mode, the biological signal measuring apparatus 10 can measure the pulse wave except when the living tissue 500 of the subject is pressed, and therefore may measure the SpO2 and the pulse rate and display them. The means for switching the pulse oximeter mode to the capillary refilling time measurement mode is not limited to the pushing down of the measurement button 26a by the user, and the switching may be performed by other switching means.

In the biological signal measuring apparatus 10 of the embodiment, when the menu button 26d is pushed down, a menu for changing various settings of the biological signal measuring apparatus 10 can be referred, and, when the lighting/determination button 26e is pushed down, a specific item can selected in the menu so as to change the setting. When the menu is not called up by means of the menu button 26d, a backlight for the display screen of the display 24 is turned on by pushing down the lighting/determination button 26e.

In the above, the functions of the portions of the biological signal measuring apparatus 10 have been schematically described. Next, the operation which is conducted in the CPU 23 until the arterial oxygen saturation and the capillary refilling time are calculated will be described in more detail. Based on the electric signals respectively corresponding to the reception light intensities of R and IR supplied from the pulse wave demodulating circuit 28 through the A/D converter 29, the CPU 23 detects periodic variation components of the reception light intensities of R light and IR light, and calculates the blood oxygen saturation (arterial oxygen saturation) of the artery in the living tissue 500 of the subject.

The calculation of the arterial oxygen saturation in the CPU 23 may be performed by any related-art method. For example, the CPU 23 separates each of the electric signals respectively corresponding to the reception light intensities of R light and IR light, into AC and DC components, and calculates the arterial oxygen saturation based on the attenuation ratio (AC/DC) which is acquired on the basis of R and IR. The CPU further calculates the pulse rate from the AC component which reflects the artery.

Furthermore, the CPU 23 calculates the capillary refilling time based on the electric signals which are supplied from the pulse wave demodulating circuit 28 through the A/D converter 29. More specifically, when the skin of the finger of the subject inserted into the probe 30 is externally pressed to cause a pressed state, the blood flow flowing through the capillary in the finger is significantly lowered. When the pressing is stopped (the pressed state is released), the blood flow which again flows through the capillary is increased as time progresses, and returns to the state which is attained before the pressing.

By the change of the blood flow in the capillary when the living tissue 500 of the subject is released from the pressed state as described above, the reception light intensities (transmitted light quantities) of R light and IR light which are transmitted through the living tissue 500 are changed. The changes of the transmitted light quantities appear as changes of the values (voltages) of the electric signals supplied from the pulse wave demodulating circuit 28 to the CPU 23 through the A/D converter 29. The CPU 23 detects the changes, and calculates the capillary refilling time.

Hereinafter, while exemplifying measurement waveforms appearing during the measurement by the biological signal measuring apparatus 10, the procedure of measuring the arterial oxygen saturation, the pulse rate, and the capillary refilling time by using the biological signal measuring apparatus 10 will be specifically described.

Figure 3:
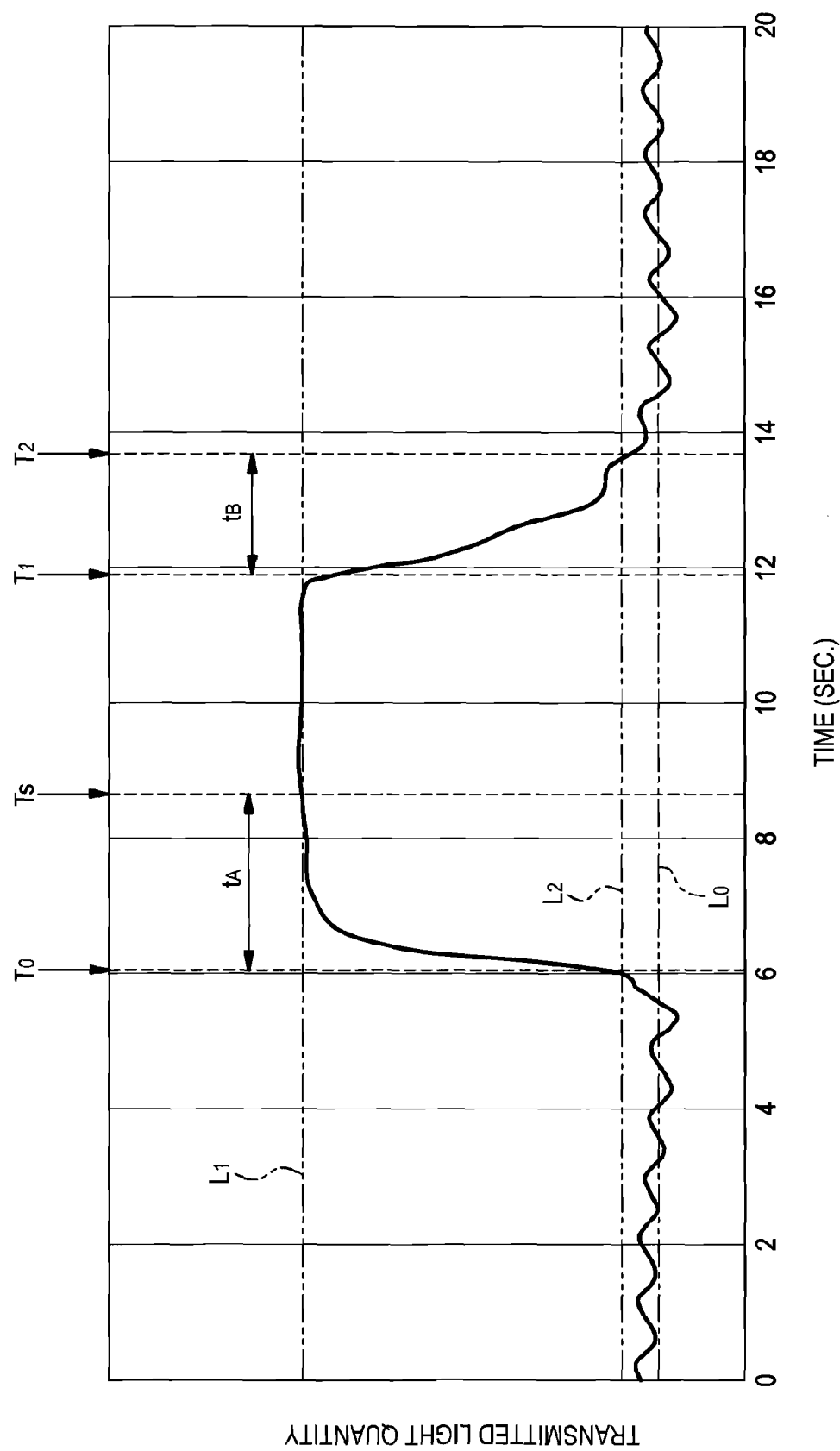
FIG. 3 is a view showing an example of a time waveform corresponding to IR among measurement waveforms acquired by the biological signal measuring apparatus.
Figure 4:
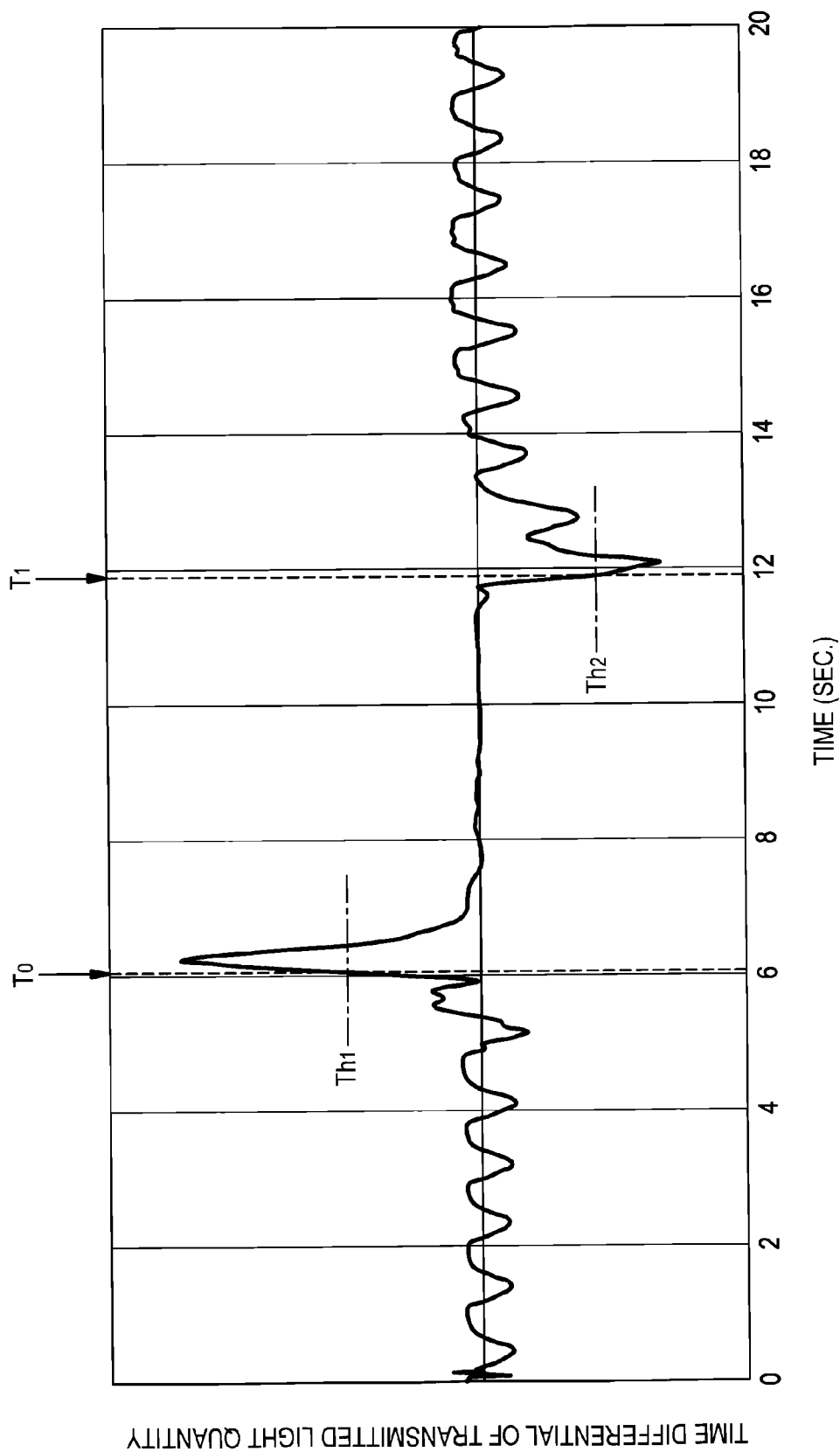
FIG. 4 is a view showing a temporal change of a value which is acquired by time-differentiating the waveform of FIG. 3.
Figure 5:
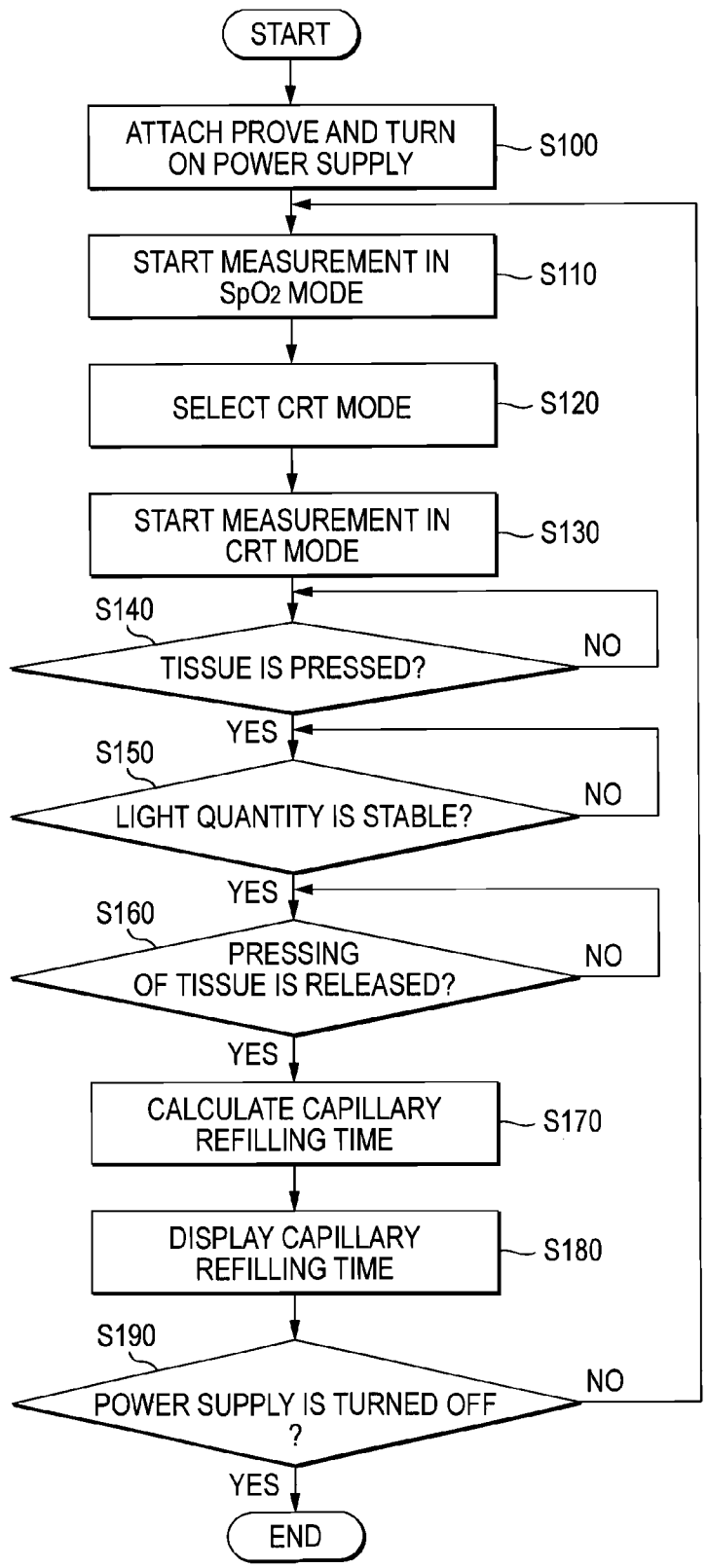
FIG. 5 is a view showing an example of a procedure of measuring the arterial oxygen saturation, the pulse rate, and the capillary refilling time by using the biological signal measuring apparatus.
Figure 6:
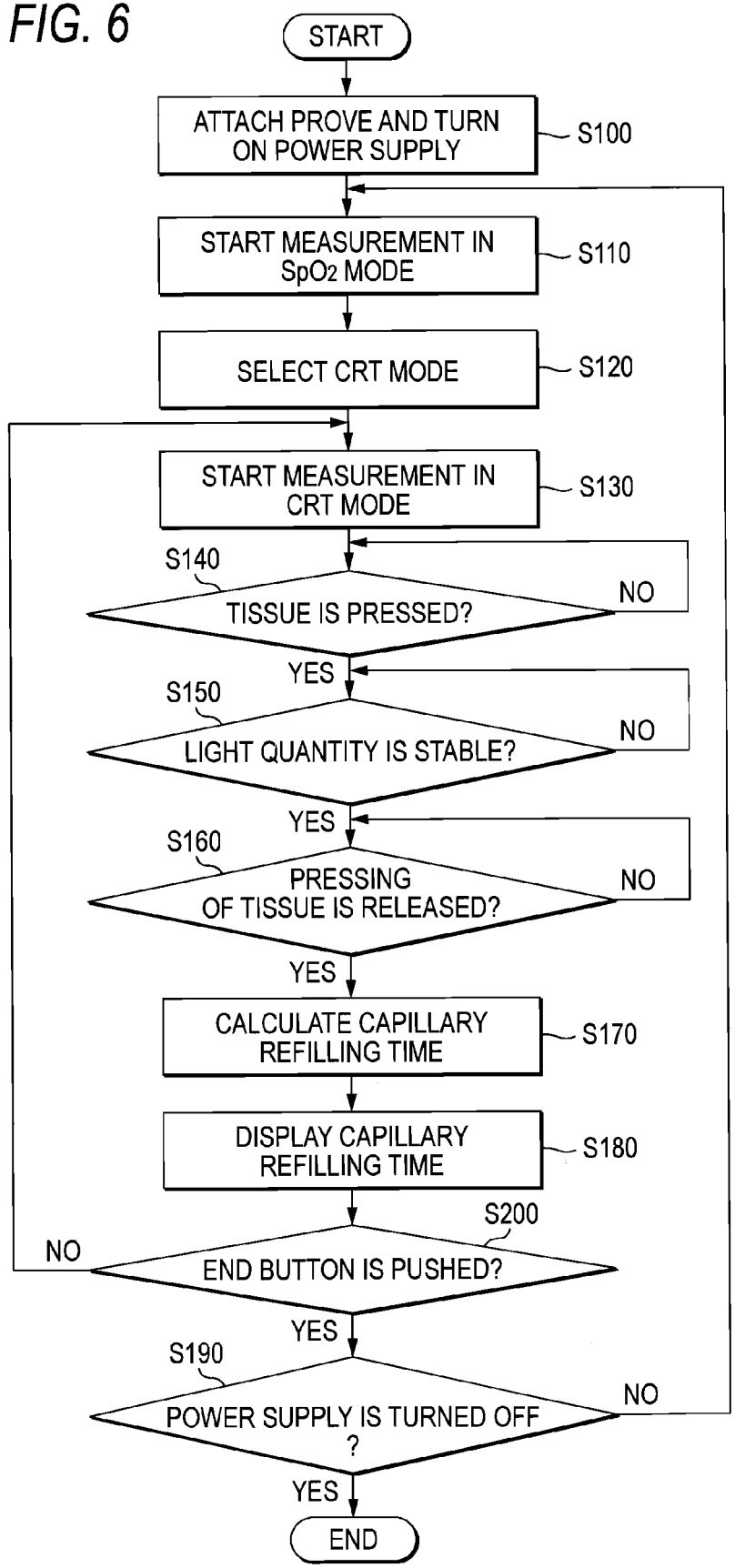
FIG. 6 is a view showing an example of a flow of a measurement procedure in the case where the mode of the biological signal measuring apparatus can be switched depending on whether an end button is pushed down after the capillary refilling time is displayed on a display or not.
Figure 7:
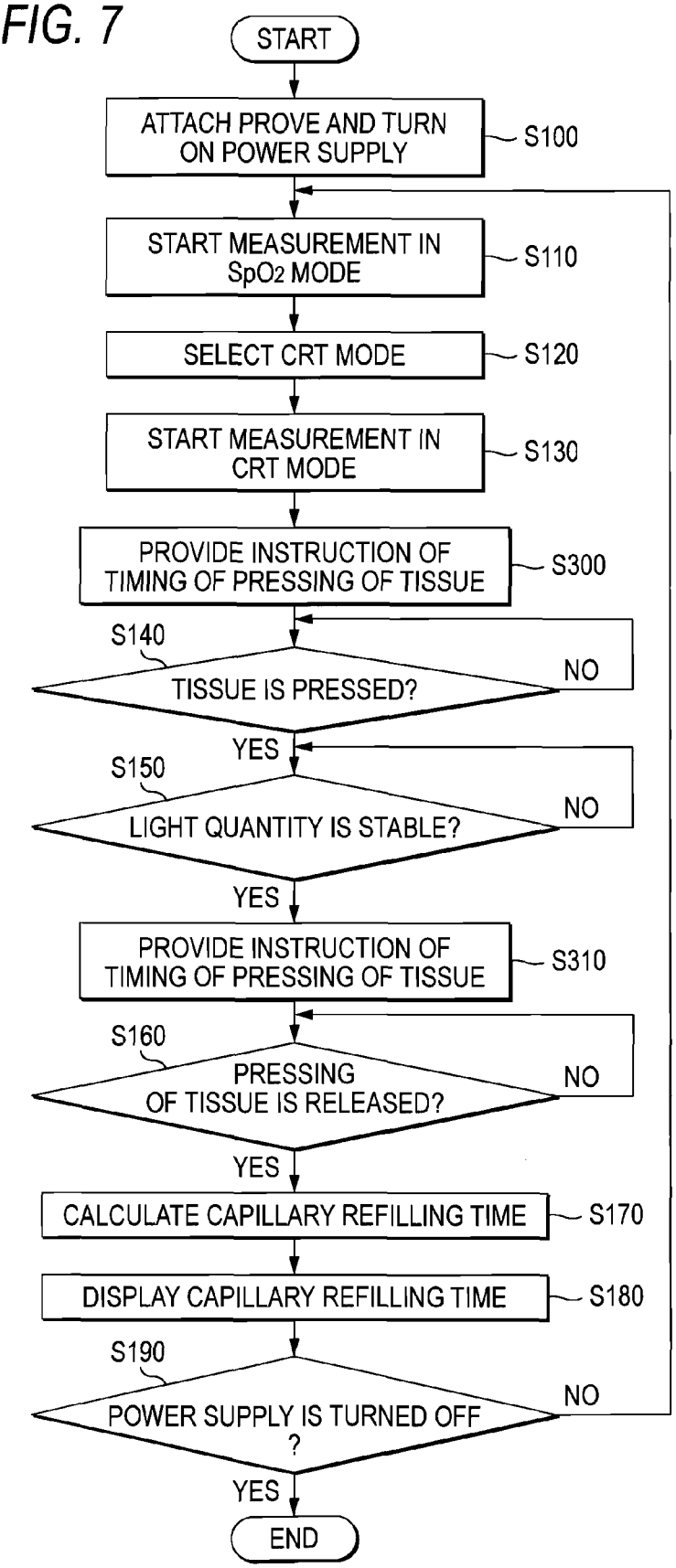
FIG. 7 is a view showing an example of a flow of a measurement procedure in the case where the biological signal measuring apparatus can instruct the user a timing when living tissue of the subject is pressed, or that when the pressing is released.

FIG. 3 shows an example of a time waveform corresponding to IR among measurement waveforms acquired by the biological signal measuring apparatus 10, and FIG. 4 shows a temporal change of a value which is acquired by time-differentiating the waveform of FIG. 3. Although a pulse wave is drawn in FIG. 3, the capillary refilling time may be calculated after pulsation components are removed by performing moving average or notch filtering. In this case, it is possible to acquire a stable measurement result which is not affected by pulsation. FIGS. 5 to 7 show an example of a procedure of measuring the arterial oxygen saturation, the pulse rate, and the capillary refilling time by using the biological signal measuring apparatus 10. In the procedure which will be described, the user may be identical with the subject.

First, the measurement procedure shown in the flow of FIG. 5 will be described. When the arterial oxygen saturation, the pulse rate, and the capillary refilling time are to be measured by using the biological signal measuring apparatus 10, the user first attaches the probe 30 to the finger (living tissue 500) of the subject, and then turns on the power supply (not shown) of the apparatus body unit 20 (step S100). Then, the biological signal measuring apparatus 10 starts to measure the transmitted light quantity in the pulse oximeter mode (SpO$_2$ mode) which is set by default (step S110), and measures the pulse rate and arterial oxygen saturation of the subject. The arterial oxygen saturation of the subject is displayed in the arterial oxygen saturation display window 24a, and the pulse rate is displayed in the pulse rate display window 24b.

When the arterial oxygen saturation of the subject is measured, the user pushes down the measurement button 26a to select the capillary refilling time measurement mode (CRT mode) (step S120). This causes the biological signal measuring apparatus 10 to start the measurement of the transmitted light quantity in the capillary refilling time measurement mode (step S130). When the measurement is started in the capillary refilling time measurement mode, the biological signal measuring apparatus 10 first detects whether the portion of the finger (living tissue 500) of the subject to which the probe 30 is attached is pressed by the user or not (step S140). More specifically, when the living tissue 500 of the subject is pressed at the timing of 5 to 6 sec. in the time axis which is shown as the abscissa in FIG. 3, the blood flow through the capillary is lowered as described above and the transmitted light quantity (the value of the electric signal corresponding to the quantity) of the living tissue 500 is rapidly increased. If it is detected that the time differential of a variation of the transmitted light quantity exceeds predetermined threshold "Th$_1$" at time "T$_o$" as shown in FIG. 4, the biological signal measuring apparatus 10 (CPU 23) determines that the living tissue 500 is pressed at time "T$_o$". The level of threshold "Th$_1$" may be set to a desired value in accordance with the detection sensitivity of the pressed state or the like. In place of the time differential, the biological signal measuring apparatus 10 (CPU 23) may set the state where the transmitted light quantity (the level of the reception light intensity) exceeds a preset threshold, as the detection conditions of the pressing of the living tissue 500.

If the pressing of the living tissue 500 is detected (step S140: YES), the biological signal measuring apparatus 10 determines whether the transmitted light quantity is stable in the pressed state or not (step S150). The determination will be described specifically by exemplifying the waveform shown in FIG. 3. At time "T$_s$" when time width "t$_A$" has elapsed from time "T$_o$" when the pressing of the living tissue 500 is detected, the biological signal measuring apparatus 10 (CPU 23) determines that the transmitted light quantity of IR is stable in the pressed state. Then, the biological signal measuring apparatus 10 displays a message indicating that the measurement of the capillary refilling time is enabled, in the status display window 24d of the display screen of the display 24 (for example, message "Standby" or the like is displayed as sown in FIG. 1). As described above, the conditions that the biological signal measuring apparatus 10 (CPU 23) determines that the living tissue 500 is in the stable pressed state are not particularly limited. For example, the variation width during a constant time period or the like may be set as the conditions.

If it is determined in step S150 that the transmitted light quantity is stable in the pressed state (step S150: YES), the biological signal measuring apparatus 10 determines whether the living tissue 500 is released from the pressed state or not (step S160). More specifically, when the living tissue 500 is released from the pressed state, the blood flow through the capillary is increased, and, in accordance with this, the quantity of light which is transmitted through the living tissue 500 is reduced. In the waveform shown in FIG. 3, for example, the living tissue 500 of the subject is released from the pressed state at the timing of 11 to 12 sec., and, at this time, the transmitted light quantity of the living tissue 500 is rapidly reduced in accordance with the increase of the blood flow through capillary. If such a reduction of the transmitted light quantity is detected, the biological signal measuring apparatus 10 determines that the living tissue 500 is released from the pressed state.

If it is determined in step S160 that the living tissue 500 is released from the pressed state (step S160: YES), the biological signal measuring apparatus 10 calculates the capillary refilling time (step S170). More specifically, for example, the biological signal measuring apparatus 10 calculates the time which, after the detection that the living tissue 500 is released from the pressed state, is required for the transmitted light quantity to be reduced to a predetermined rate with respect to the difference between reception light intensities before and after the pressing of the living tissue 500, as the capillary refilling time. The flow of calculating the capillary refilling time by using the biological signal measuring apparatus 10 will be described later in more detail.

The capillary refilling time which is calculated in step S170 is displayed in the capillary refilling time display window 24c of the display 24 (step S180). When the power supply of the apparatus body unit 20 is then turned off (step S190: YES), the measurement is ended. In a state where the power supply is on, after the value of the capillary refilling time is displayed on the display 24, the mode is automatically switched to the pulse oximeter mode, and the measurement of the transmitted light quantity is started in the pulse oximeter mode (step S110).

If the pressing of the living tissue 500 is not detected in step S140 (step S140: NO), the biological signal measuring apparatus 10 is set to the standby state until the pressing of the living tissue 500 is detected in the capillary refilling time measurement mode. Until it is determined in step S150 that the transmitted light quantity is stable in the pressed state (step S150: NO), the biological signal measuring apparatus 10 continues to repeat the calculation for comparing the conditions for determining stabilization with the transmitted light quantity. Until it is determined in step S160 that the living tissue 500 is released from the pressed state (step S160: NO), moreover, the biological signal measuring apparatus 10 continues to repeat the calculation for comparing the conditions for detecting release from the pressed state with the transmitted light quantity.

In the measurement procedure, the user manually switches the mode from the pulse oximeter mode to the capillary refilling time measurement mode. Alternatively, the mode may be automatically switched. For example, the biological signal measuring apparatus 10 (CPU 23) may be automatically switched from the pulse oximeter mode to the capillary refilling time measurement mode at the timing when, in step S140 of the measurement procedure, it is detected that the time differential of a variation of the transmitted light quantity exceeds threshold "Th$_1$" shown in FIG. 4.

In the flow, after the value of the capillary refilling time is displayed in step S180 on the display 24, the mode is automatically switched to the pulse oximeter mode. Depending on whether the end button 26b is pushed down after the display on the display 24 is performed or not, for example, it is possible to select whether the mode is to be switched to the pulse oximeter mode or not. FIG. 6 shows an example of a flow of a measurement procedure in the case where the mode of the biological signal measuring apparatus 10 can be switched depending on whether the end button 26b is pushed down after the capillary refilling time is displayed on the display 24 or not. In the flow shown in FIG. 6, the steps which are common to those of the flow shown in FIG. 5 are denoted by the same reference numerals, and their description will be omitted.

In the embodiment, in the case where the end button 26b is pushed down after the display on the display 24 is performed (step S200: YES), if the mode is again switched to the pulse oximeter mode and the power supply is not turned off (step S190: NO), the measurement of the transmitted light quantity is started in the pulse oximeter mode (step S110). By contrast, if the end button 26b is not pushed down after the display on the display 24 is performed (step S200: NO), the measurement of the transmitted light quantity is again started in the capillary refilling time measurement mode (step S130). In the biological signal measuring apparatus 10, the pulse oximeter mode and the capillary refilling time measurement mode may be simultaneously performed. In the state where the living tissue 500 is pressed, however, the measurement values of the arterial oxygen saturation and the pulse rate in the pulse oximeter mode often exhibit abnormal values. Therefore, it is preferable that one of the pulse oximeter mode and the capillary refilling time measurement mode is exclusively performed.

FIG. 7 shows an example of a flow of a measurement procedure in the case where the biological signal measuring apparatus 10 can instruct the user a timing when the living tissue 500 of the subject is pressed, or that when the pressing is released. In the flow showing in FIG. 7, the steps which are common to those of the flow shown in FIG. 5 or 6 are denoted by the same reference numerals, and their description will be omitted. In the embodiment, the biological signal measuring apparatus 10 includes means for transmitting visually or audibly information to the user, such as an alarming device or a warning lamp. For example, the biological signal measuring apparatus 10 starts the measurement of the transmitted light quantity in the capillary refilling time measurement mode (step S130), and thereafter instructs the user the timing when the living tissue 500 of the subject is pressed (step S300). If it is determined that the transmitted light quantity is stable in the pressed state (step S150: YES), the biological signal measuring apparatus 10 counts the elapsed time from this, and, after elapse of a predetermined time, instructs the user the timing when the pressing is released (step S310). In measurement of the capillary refilling time, usually, the pressing time is set to 5 sec. Therefore, the predetermined time is usually set to about 5 sec., but it is preferable that the user can set the predetermined time. Since the biological signal measuring apparatus 10 has the above-described function, the burden of time measurement on the subject can be reduced, and measurement which is more accurate can be performed.

Here, the flow of calculating the capillary refilling time in step S170 will be described with reference to FIG. 8. In the calculation of the capillary refilling time by the biological signal measuring apparatus 10, first, the CPU 23 reads the data of the transmitted light quantity which are measured in a preset time range from a predetermined timing, from the storage 25 (step S171).

Here, the predetermined timing may be the timing when the measurement button 26a is pushed in step S120, or the timing preceding the time ($T_o$) when the CPU 23 detects the start of the pressing of the living tissue 500 as described later, by a constant time. The time range includes a sufficiently long time before the pressing of the living tissue 500, and also the time which extends from the start of the pressing to the timing when the pressed state is stable.

Then, the CPU 23 specifies the transmitted light quantity before the pressing of the living tissue 500, from the measurement data read from the storage 25 (step S173). In the embodiment, the CPU 23 calculates an averaged value of the measurement data before $T_o$, as the transmitted light quantity before the pressing of the living tissue 500.

Next, the CPU 23 specifies the transmitted light quantity in the pressed state of the living tissue 500 (step S175). In the embodiment, in the measurement data read from the storage 25, the CPU 23 calculates an averaged value of the measurement data after time "$T_s$", as the transmitted light quantity in the pressed state of the living tissue 500. Measurement data which are subjected to notch filtering centered at frequency components of the temporal variations (pulse waves) of the reception light intensities in the state before the pressing of the living tissue and the pressed state may be set as the transmitted light quantity in the pressed state.

Next, the CPU 23 calculates the difference between the transmitted light quantity in the state where the living tissue 500 is pressed, and that before the pressing of the living tissue 500, as an increment of the transmitted light quantity due to the pressing of the living tissue 500, and also the time which is elapsed from the timing when the living tissue 500 is released from the pressed state, to that when the transmitted light quantity attenuates to a predetermined ratio with respect to the increment, as the capillary refilling time (step S177). For example, the predetermined ratio is preferably 90%. In the case where the capillary refilling time is very long, however, the predetermined ratio may be set to a smaller value such as 70%.

As shown in 12 to 14 sec. in the time axis which is shown as the abscissa in FIG. 3, in accordance with the increase of the blood flow of capillary due to the release of the pressed state, the transmitted light quantity is rapidly reduced. When the time differential of a variation of the transmitted light quantity becomes less than predetermined threshold "$Th_2$" at time "$T_1$" as shown in FIG. 4, the CPU 23 detects that the living tissue 500 is released from the pressed state at time "$T_1$". The level of threshold "$Th_2$" may be set to a desired value in accordance with the detection sensitivity in the detection of the release from the pressed state, or the like. In place of the time differential, the CPU 23 may set the state where the transmitted light quantity (the level of the reception light intensity) becomes less than a preset threshold, as the detection conditions of the release of the living tissue 500 from the pressed state.

If it is detected that the living tissue 500 is released from the pressed state, the CPU 23 continues to detect the temporal change of the transmitted light quantity of IR, and specifies time "$T_2$" when the transmitted light quantity of IR attenuates to 90% of the transmitted light quantity calculated in step S175 (the transmitted light quantity in the state where the living tissue 500 is pressed). Then, the CPU 23 calculates elapsed time "$t_B$" from time "$T_1$" to time "$T_2$" as the capillary refilling time. Then, the flow of calculating the capillary refilling time by the CPU 23 is ended.

In the biological signal measuring apparatus 10 of the embodiment, in the case where the detected transmitted light quantity is increased by pressing of the living tissue 500 to exceed the upper limit of the detection sensitivity of the transmitted light quantity before the pressing of the living tissue 500 (during the measurement of the arterial oxygen saturation), the detection sensitivity of the transmitted light quantity may be changed to a range where the transmitted light quantity in the pressed state of the living tissue 500 can be detected. At the timing (time "$T_o$" shown in FIG. 4) when the time differential of a variation of the transmitted light quantity exceeds predetermined threshold "$Th_1$", for example, the CPU 23 may change the detection sensitivity of the transmitted light quantity as described above. In this case, the CPU 23 may correct the detection data of the transmitted light quantity in accordance with the change of the detection sensitivity.

In the biological signal measuring apparatus 10 of the embodiment, the CPU 23 may change the detection sensitivity of the transmitted light quantity in accordance with that the measurement button 26a of the apparatus body unit 20 is pressed in step S110, as described above. In the embodiment, the CPU 23 maintains the detection sensitivity of the transmitted light quantity constant, during a period from the change of the detection sensitivity to the end of the calculation of the capillary refilling time.

In the biological signal measuring apparatus 10 of the embodiment, in the case where the capillary refilling time is calculated, the CPU 23 determines whether the capillary refilling time (newly calculated value) satisfies predetermined reject conditions or not. More specifically, for example, the CPU 23 reads out a plurality of capillary refilling times (already calculated values) which have been calculated, from the storage 25, and compares them with the newly calculated value. When the newly calculated value is different from the average of the already calculated values by a predetermined width or more, for example, the CPU 23 displays the average of the already calculated values on the display 24. In this case, the CPU 23 may display a display (measurement error display) indicating that the newly calculated value is a value in which a measurement error is suspected, together with the average on the display 24.

In the case where there is only one already calculated value of the capillary refilling time, the user may determine whether the newly calculated value is a value in which a measurement error is suspected or not. In this case, in response to a rejecting operation by the user, the newly calculated value may be displayed on the display 24 together with the measurement error display. In the case where there are two or more already calculated values, for example, the calculated values and the average may be displayed on the display 24, and, among the calculated values, a rejected value may be displayed together with the measurement error display. In this case, alternatively, the average of the calculated values excluding the rejected value may be displayed on the display 24.

Together with the measurement waveform, time width selection information for selecting, by the user, time width corresponding to a specific part in the time axis of the measurement waveform may be displayed on the display 24. More specifically, as shown in FIG. 9, cursors A and B which are movable in the direction of the time axis in response to the operation by the user may be displayed in the measurement waveform that is displayed in the display 24. In the embodiment, when the user operates the operation acceptor 26 to move the cursors A and B to both ends of a part of the measurement waveform, time width of which the user wants to know, displayed in the display 24, the CPU 23 calculates the time width $t_x$ between the part both ends of which are indicated by the cursors A and B.

The CPU 23 outputs the calculated time width $t_x$ to the display 24 and displays it on the display 24, in real time. In place of the configuration, a configuration may be employed where the calculated time width $t_x$ is displayed on the display 24 only when the user performs a predetermined operation for displaying it through the operation acceptor 26. Since the biological information measuring apparatus 10 is provided with the function capable of calculating a time width in a specific part of the measurement waveform in response to the operation by the user, the user can select time width which is assumed as appropriate capillary refilling time and calculate the time width in a case, for example, where well-defined noise is mixed in the measurement waveform and the appropriate capillary refilling time cannot be acquired. In the embodiment, as shown in FIG. 9, the method of selecting the time width by moving the cursors is described as one example of the time width selection information. However, the method of selecting the time width is not limited to the cursors. The time width may be selected by moving points (not shown) displayed on the display 24.

In the biological signal measuring apparatus 10 of the embodiment, in the case where the detection sensitivity of the transmitted light quantity is changed as described above, the CPU 23 displays the temporal waveform of the transmitted light quantity which is corrected in accordance with the change of the detection sensitivity, on the display 24. Although not illustrated, in addition to the temporal waveform of the transmitted light quantity, the display 24 may display the time ($T_o$) when the pressing of the living tissue 500 is detected, the time ($T_s$) when the pressed state is determined to be stable, the time ($T_1$) when the living tissue 500 is determined to be released from the pressed state, the time ($T_2$) when the living tissue 500 is determined to be refilled, and the like. Since the display 24 has the function of displaying these times, the user can perform the measurement while checking the state where stable pressing is applied, through the display, and, after the measurement is ended, check the right/wrong of the measurement result. Although not illustrated, the biological signal measuring apparatus 10 may include means for instructing the user timings of pressing tissue and releasing the pressing by a visual or auditory manner such as that a sound or a voice message is output, or that light is emitted, as one function of the biological signal measuring apparatus 10 (CPU 23).

The probe 30 may be provided with a pressure sensor (not shown) having a thin film-like shape. In the case that the capillary refilling time measurement mode is selected, when the living tissue 500 is pressed, the pressure sensor detects a timing when the living tissue 500 is in the pressed state and a timing when the living tissue 500 is released from the pressed state. The pressure sensor may transmit the detected timing to the CPU 23. The CPU 23 performs the calculation by using the timing received from the pressure sensor, thereby the accuracy of the calculation of the capillary refilling time is improved. In the case that the pulse oximeter mode is selected, the pressure sensor detects a pressure by detecting the above-described timing, it may be determined that the noise is mixed in the waveform and the processing may be performed to remove the noise. The pressure sensor is not limited to the thin film-like pressure sensor and it is not necessarily provided with the probe. The pressure sensor may be replaced with any other type of sensor which can detect the timing when the living tissue 500 is in the pressed state and the timing when the living tissue 500 is released from the pressed state.

In the biological signal measuring apparatus 10 of the embodiment, as described above, also the capillary refilling time can be measured in addition to measurement of the arterial oxygen saturation. In an emergency situation or the like, therefore, the condition of the patient can be checked more accurately and rapidly. In the case where measurement is to be performed on a finger tip or the like, release from the state where the finger tip is pressed is detected, and the capillary refilling time is automatically measured. Therefore, the capillary refilling time can be measured quantitatively and objectively while eliminating the subjectivity of the user, and an error due to the technique or determination of the user hardly occurs in the calculation result of the capillary refilling time.

In the biological signal measuring apparatus 10 of the embodiment, moreover, the difference between the averaged values of variations of the transmitted light quantities in the states before and after the pressing on the living tissue 500 is used in the measurement of the capillary refilling time, and hence it is possible to measure the capillary refilling time in which the pulse wave component and the like are canceled out. In the biological signal measuring apparatus 10 of the embodiment, in the case where a newly measured capillary refilling time is largely different from previously measured ones, furthermore, the new measurement result in which a measurement error is suspected is not displayed, and an average of the previous measurement result is displayed, so that a diagnosis error hardly occurs.

Although the invention has been described using the embodiment, the technical scope of the invention is not restricted to the scope of the description of the embodiment. It is obvious to those skilled in the art that various changes or improvements can be made on the embodiment.

According to as aspect of the invention, in addition to measurement of the blood oxygen saturation which is performed on most of emergency patients by using a pulse oximeter, also the capillary refilling time can be measured by using the same apparatus. Therefore, the user is puzzled about the operation of the apparatus, and can check the condition of the patient more accurately and rapidly in an emergency situation or the like. In the case where measurement is to be performed on a finger tip or the like, release from the state where the finger tip is pressed is automatically detected, and the time required for reduction to a preset rate with respect to the difference between reception light intensities before and after the pressing of the finger tip is measured. Therefore, the capillary refilling time can be measured quantitatively and objectively while eliminating the subjectivity of a user, and a measurement error hardly occurs.

According to an aspect of the invention, only one of the pulse oximeter mode and the capillary refilling time measurement mode is selected, and then measurement is performed. During measurement of the capillary refilling time, therefore, the blood oxygen saturation and the pulse rate are not measured, and hence an alarm or the like indicating an abnormal value of the blood oxygen saturation or the pulse rate due to pressing of the patient is not issued. In the biological signal measuring apparatus of the invention, moreover, a variation of the reception light intensity can be displayed by the display. Therefore, it is possible to easily conduct a visual check whether the measurement of the capillary refilling time is adequately performed or not.

Since the value which is acquired by averaging variations of the reception light intensities in states before and after the pressing is used in the calculation of the difference of the reception light intensities, it is possible to measure the capillary refilling time in which the pulse wave component and the like are canceled out. In the case where a newly measured capillary refilling time is largely different from previously measured ones, the new measurement result in which a measurement error is suspected is not displayed, and an average of the previous measurement result is displayed, so that a diagnosis error hardly occurs.

What is claimed is:

1. A biological signal measuring apparatus comprising:
   a probe which is adapted to be attached to living tissue of a subject and adapted to be externally pressed to cause a pressed state to the living tissue;
   a light emitter which emits at least two light beams having different wavelengths to the living tissue of the subject;
   a light receiver which receives the light beams that are emitted from the light emitter and transmitted through or reflected from the living tissue, and which converts at least one of the light beams to at least one electric signal that corresponds to a reception light intensity of the at least one of the light beams;
   a detector which detects temporal variation of the reception light intensity from the electric signal;
   a selector which selects based upon data analysis one of (i) a pulse oximeter mode in which at least one of an oxygen saturation and a pulse rate is calculated and (ii) a capillary refilling time measurement mode in which a capillary refilling time is calculated; and
   a calculator which, based on the temporal variation of the reception light intensity, performs a calculation in the mode that is selected by the selector,
   wherein the capillary refilling time measurement mode is automatically selected only when measured data is indicative that the living tissue of the subject enters the pressed state; and
   wherein the capillary refilling time measurement mode remains selected until (i) the living tissue of the subject is released from the pressed state and (ii) the capillary refilling time is calculated by the calculator based upon a detectable signal obtained subsequent to the subject being released from the pressed state.

2. The biological signal measuring apparatus according to claim 1, wherein the calculator detects that the living tissue is released from the pressed state in which the living tissue is pressed, in accordance with that a level of the reception light intensity or a time differential of a temporal reduction of the reception light intensity becomes less than a predetermined threshold.

3. The biological signal measuring apparatus according to claim 2, wherein, in a case where the capillary refilling time measurement mode is selected, the calculator calculates, as the capillary refilling time, a time which, after detecting that the living tissue is released from the pressed state, is required for the reception light intensity to be reduced to a predetermined rate with respect to a difference between levels of the reception light intensity before and after the living tissue is pressed.

4. The biological signal measuring apparatus according to claim 3, wherein the calculator averages a variation of the reception light intensity in a predetermined time in each of the pressed state and a state before the living tissue is pressed, and calculates, as the difference, a difference between the averaged variation in the pressed state and the averaged variation in the state before the living tissue is pressed.

5. The biological signal measuring apparatus according to claim 1, wherein the calculator applies notch filtering centered at frequency components of a pulse wave on a variation of the reception light intensity in a predetermined time.

6. The biological signal measuring apparatus according to claim 1, wherein the calculator changes a detection sensitivity of the electric signal so that the electric signal can be detected in the pressed state, in accordance with that a level of the reception light intensity or a time differential of a temporal increase of the reception light intensity exceeds a predetermined threshold.

7. The biological signal measuring apparatus according to claim 6, wherein the calculator maintains the detection sensitivity constant during a period from a time when the detection sensitivity is changed to a time when the capillary refilling time is calculated.

8. The biological signal measuring apparatus according to claim 6, wherein, in a case where the detection sensitivity is changed, the calculator corrects the temporal variation of the reception light intensity before the detection sensitivity is changed to the temporal variation of the reception light intensity after the detection sensitivity is changed.

9. The biological signal measuring apparatus according to claim 1, further comprising a display which displays the capillary refilling time and the temporal variation of the reception light intensity.

10. The biological signal measuring apparatus according to claim 9, wherein, in a case where a plurality of the capillary refilling time are calculated, under a condition that one of the plurality of the capillary refilling time which is newly calculated satisfies a predetermined reject condition, the calculator displays an average of the other of the plurality of the capillary refilling time, as a latest capillary refilling time on the display.

11. The biological signal measuring apparatus according to claim 9, wherein
the display displays a time waveform indicating the temporal variation of the reception light intensity and information for selecting time width corresponding to a part of the time waveform, and
the calculator calculates the time width based on the information displayed on the display.

12. The biological signal measuring apparatus according to claim 1, further comprising a pressure sensor which detects at least one of a timing when the living tissue is pressed and a timing when the pressed state in which the living tissue is pressed is released,
wherein the calculator performs the calculation based on the temporal variation of the reception light intensity and the timing that is detected by the pressure sensor.

13. A biological signal measuring apparatus comprising:
a probe which is adapted to be attached to living tissue of a subject and adapted to be externally pressed to cause a pressed state to the living tissue;
a light emitter which emits at least two light beams having different wavelengths to the living tissue of the subject;
a light receiver which receives the light beams that are emitted from the light emitter and transmitted through or reflected from the living tissue, and which converts at least one of the light beams to at least one electric signal that corresponds to a reception light intensity of the at least one of the light beams;
a detector which detects temporal variation of the reception light intensity from the electric signal;
a selector which selects one of (i) a pulse oximeter mode in which at least one of an oxygen saturation and a pulse rate is calculated and (ii) a capillary refilling time measurement mode in which a capillary refilling time is calculated;
a calculator which, based on the temporal variation of the reception light intensity, performs a calculation in the mode that is selected by the selector; and
an operation acceptor which accepts an operation of starting measurement of the capillary refilling time,
wherein the calculator changes a detection sensitivity of the electric signal so that the electric signal can be detected in the pressed state, in accordance with that the operation acceptor accepts the operation of starting measurement of the capillary refilling time.

14. The biological signal measuring apparatus according to claim 13, wherein the calculator maintains the detection sensitivity constant during a period from a time when the detection sensitivity is changed to a time when the capillary refilling time is calculated.

15. The biological signal measuring apparatus according to claim 13, wherein, in a case where the detection sensitivity is changed, the calculator corrects the temporal variation of the reception light intensity before the detection sensitivity is changed, to the temporal variation of the reception light intensity after the detection sensitivity is changed.

16. A biological signal measuring apparatus comprising:
a probe which is adapted to be attached to living tissue of a subject and adapted to be externally pressed to cause a pressed state to the living tissue;
a light emitter which emits at least two light beams having different wavelengths to the living tissue of the subject;
a light receiver which receives the light beams that are emitted from the light emitter and transmitted through or reflected from the living tissue, and which converts at least one of the light beams to at least one electric signal that corresponds to a reception light intensity of the at least one of the light beams;
a detector which detects temporal variation of the reception light intensity from the electric signal;
a selector which selects one of (i) a pulse oximeter mode in which at least one of an oxygen saturation and a pulse rate is calculated and (ii) a capillary refilling time measurement mode in which a capillary refilling time is calculated; and
a calculator which, based on the temporal variation of the reception light intensity, performs a calculation in the mode that is selected by the selector, wherein,
an upper limit of a detection sensitivity of the electric signal when the pulse oximeter mode is selected is less than the electric signal that corresponds to the reception light intensity when the living tissue is pressed, and
when the mode is changed from the pulse oximeter mode to the capillary refilling time measurement mode, the calculator changes an upper limit of the detection sensitivity of the electric signal to be greater than the electric signal that corresponds to the reception light intensity when the living tissue is pressed.

17. A biological signal measuring apparatus comprising:
a probe which is adapted to be attached to living tissue of a subject and adapted to be externally pressed to cause a pressed state to the living tissue;
a light emitter which emits at least two light beams having different wavelengths to the living tissue of the subject;
a light receiver which receives the light beams that are emitted from the light emitter and transmitted through or reflected from the living tissue, and which converts at least one of the light beams to at least one electric signal that corresponds to a reception light intensity of the at least one of the light beams;
a detector which detects temporal variation of the reception light intensity from the electric signal;
a selector which selects one of (i) a pulse oximeter mode in which at least one of an oxygen saturation and a pulse rate is calculated and (ii) a capillary refilling time measurement mode in which a capillary refilling time is calculated;

a calculator which, based on the temporal variation of the reception light intensity, performs a calculation in the mode that is selected by the selector; and an instructing unit which, when the capillary refilling time measurement mode is selected, instructs the user, in a visual or auditory manner, when to press the living tissue and/or when to release pressure from the living tissue.

\* \* \* \* \*